(12) United States Patent
Jeong et al.

(10) Patent No.: US 11,446,223 B2
(45) Date of Patent: Sep. 20, 2022

(54) ANTI-AGING COMPOSITION

(71) Applicant: NEOPHARM CO., LTD., Daejeon (KR)

(72) Inventors: Se Kyoo Jeong, Daejeon (KR); Bu-Mahn Park, Daejeon (KR); Kyung Sook Yoo, Daejeon (KR); Sung Woo Kim, Daejeon (KR); Hye Seong Shin, Ulsan (KR)

(73) Assignee: NEOPHARM CO., LTD., Daejeon (KR)

( * ) Notice: Subject to any disclaimer, the term of this patent is extended or adjusted under 35 U.S.C. 154(b) by 850 days.

(21) Appl. No.: 16/095,765

(22) PCT Filed: Apr. 7, 2017

(86) PCT No.: PCT/KR2017/003824
§ 371 (c)(1),
(2) Date: Oct. 23, 2018

(87) PCT Pub. No.: WO2017/188623
PCT Pub. Date: Nov. 2, 2017

(65) Prior Publication Data
US 2020/0330352 A1    Oct. 22, 2020

(30) Foreign Application Priority Data

Apr. 27, 2016   (KR) .................... 10-2016-0051598

(51) Int. Cl.
| | | |
|---|---|---|
| *A61K 8/42* | (2006.01) |
| *A61K 31/164* | (2006.01) |
| *A61K 31/165* | (2006.01) |
| *A61K 31/404* | (2006.01) |
| *A61K 31/4164* | (2006.01) |
| *A61K 9/70* | (2006.01) |
| *A61K 8/49* | (2006.01) |
| *A61K 9/06* | (2006.01) |
| *A61Q 19/00* | (2006.01) |
| *A61K 8/02* | (2006.01) |
| *A61P 17/00* | (2006.01) |
| *A61K 8/44* | (2006.01) |
| *A61Q 19/08* | (2006.01) |
| *A61K 8/04* | (2006.01) |
| *A61K 8/19* | (2006.01) |
| *A61K 8/23* | (2006.01) |
| *A61K 8/27* | (2006.01) |
| *A61K 8/31* | (2006.01) |
| *A61K 8/368* | (2006.01) |
| *A61K 8/37* | (2006.01) |
| *A61K 8/41* | (2006.01) |
| *A61K 8/46* | (2006.01) |
| *A61K 8/58* | (2006.01) |
| *A61K 8/73* | (2006.01) |
| *A61K 8/89* | (2006.01) |
| *A61K 8/891* | (2006.01) |
| *A61Q 5/00* | (2006.01) |
| *A61Q 5/12* | (2006.01) |

(52) U.S. Cl.
CPC ............... *A61K 8/44* (2013.01); *A61Q 19/08* (2013.01)

(58) Field of Classification Search
None
See application file for complete search history.

(56) References Cited

U.S. PATENT DOCUMENTS

2012/0016032 A1*  1/2012  Moussou ............... A61K 8/365
514/574
2019/0262287 A1   8/2019  Park et al.

FOREIGN PATENT DOCUMENTS

| KR | 100341793 B1 | 6/2002 |
| KR | 1020040091116 A | 10/2004 |
| KR | 1020060053262 A | 5/2006 |
| WO | 2006049404 A1 | 5/2006 |
| WO | 2018074727 A1 | 4/2018 |

OTHER PUBLICATIONS

Aging Skin (Skinology Medical Spa, 2009). (Year: 2009).*
Northrup (Aging Skin, https://www.drnorthrup.com/ aging-skin/, 2015) (Year: 2015).*
Park, H. et al., "K6PC-5, a novel sphingosine kinase activator, improves long-term ultraviolet light-exposed aged murine skin," Experimental Dermatology, vol. 17, No. 10, Oct. 2008, Published Online Mar. 13, 2008, 8 pages.
Youm, J. et al., "K6PC-5, a sphingosine kinase activator, induces anti-aging effects in intrinsically aged skin through intracellular Ca2+ signaling," Journal of Dermatological Science, vol. 51, No. 2, Aug. 2008, Published Online Apr. 16, 2008, 14 pages.
ISA Korean Patent Office, International Search Report Issued in Application No. PCT/KR2017/003824, dated Jul. 17, 2017, WIPO, 4 pages.
CAS Registry Database Chemical Abstract No. 98552-89-7, Oct. 12, 1985, 1 page. (European Search Report Issued in Application No. 17789808.7 for Explanation of Relevancy).
CAS Registry Database Chemical Abstract No. 114214-76-5, Apr. 30, 1988, 1 page. (European Search Report Issued in Application No. 17789808.7 for Explanation of Relevancy).
Levi, M. et al., "Pharmacokinetics and Antiepileptic Activity of Valproyl Hydroxamic Acid Derivatives," Pharmaceutical Research, vol. 14, No. 2, Feb. 1997, 5 pages.
CAS Registry Database Chemical Abstract No. 1482693-14-0, Nov. 28, 2013, 1 page. (Extended European Search Report Issued in Application No. 17789808.7 for Explanation of Relevancy).

(Continued)

*Primary Examiner* — Layla Soroush
(74) *Attorney, Agent, or Firm* — McCoy Russell LLP

(57) ABSTRACT

The present invention relates to an anti-aging composition. More specifically, the anti-aging composition according to the present invention is highly stable, harmless to the body, and effective in reducing wrinkles and improving elasticity of the skin due to the superb capability for stimulating collagen biosynthesis.

2 Claims, 1 Drawing Sheet

(56) References Cited

OTHER PUBLICATIONS

CAS Registry Database Chemical Abstract No. 148513-33-2, Nov. 29, 2013, 1 page. (Extended European Search Report Issued in Application No. 17789808.7 for Explanation of Relevancy).
CAS Registry Database Chemical Abstract No. 1489868-05-4, Dec. 8, 2013, 1 page. (Extended European Search Report Issued in Application No. 17789808.7 for Explanation of Relevancy).
CAS Registry Database Chemical Abstract No. 1553451-04-9, Feb. 24, 2014, 1 page. (Extended European Search Report Issued in Application No. 17789808.7 for Explanation of Relevancy).
CAS Registry Database Chemical Abstract No. 1700080-81-4, May 7, 2015, 1 page. (Extended European Search Report Issued in Application No. 17789808 7 for Explanation of Relevancy).
European Patent Office, Extended European Search Report Issued in Application No. 17789808.7, Nov. 4, 2019, Germany, 58 pages.
Guan, L. et al., "Synthesis and Anticonvulsant Activity of N-(2-Hydroxy-ethyl)amide Derivatives," Archiv der Pharmazie, vol. 342, No. 1, Jan. 2009, 7 pages.
Japanese Patent Office, Office Action Issued in Application No. 2018-554589, dated Sep. 6, 2021, 5 pages.

* cited by examiner

ANTI-AGING COMPOSITION

CROSS-REFERENCE TO RELATED APPLICATIONS

The present application is a U.S. National Phase of International Patent Application Serial No. PCT/KR2017/003824 entitled "ANTI-AGING COMPOSITION," filed on Apr. 7, 2017. International Patent Application Serial No. PCT/KR2017/003824 claims priority to Korean Patent Application No. 10-2016-0051598, filed on Apr. 27, 2016. The entire contents of each of the above-cited applications are hereby incorporated by reference in their entirety for all purposes.

TECHNICAL FIELD

The present invention relates to an anti-aging composition, and more particularly, to an anti-aging composition for reducing skin wrinkles and improving skin elasticity, including a compound stimulating collagen biosynthesis, as an effective component.

BACKGROUND ART

Skin is an important organ responsible for various physiological functions such as a barrier function preventing moisture and useful components inside from being discharged to the outside, body temperature control, or excretion. In general, since the skin has many chances to be in contact with various external stimuli, wrinkles easily occur in the skin as compared with other organs. Particularly facial skin is directly exposed to sunlight, dry environment, pollutants, or the like, thereby being aged such as having wrinkles, earlier than the skin which is not exposed to the outside. The most characteristic change due to aging of skin tissue is a change in a skin matrix, in which human skin fibroblasts in a dermal layer are aged, which reduces the ability to produce fiber and a substrate, and an amount of the substrate is overall decreased, so that a thickness of skin is decreased to reduce skin elasticity and form wrinkles. That is, as aging proceeds, decreased elasticity, blood circulation disorder, weakening of a skin barrier, and the like of the skin becomes even more severe.

Recently, after introduction of functional cosmetics into the Republic of Korea, importance of new material development was highlighted, and functional new materials have been actively developed, however, there are not many functional anti-aging raw materials for reducing skin wrinkles and improving skin elasticity which have been actually commercialized. A research direction for reducing skin wrinkles may be classified into the followings: removing environmental factors accelerating skin aging such as ultraviolet rays, active oxygen and dry skin to delay skin aging itself; preparing prevention measures such as inhibition of elastinase, biosynthesis acceleration and decomposition inhibition of collagen, and synthesis acceleration of hyaluronic acid, based on the research results for a creation mechanism of skin wrinkles; and directly injecting collagen or hyaluronic acid to alleviate created skin wrinkles, supplementing reduced skin matrix components or cells to improve produced skin wrinkles, or the like.

Currently the most representative anti-aging functional raw material for reducing skin wrinkles and improving skin elasticity includes retinoids, vitamin C, and the like. Among the retinoids, retinoic acid is used as a powerful anti-aging therapeutic agent, however, has strong irritation to the skin, thereby being limitedly used as a therapeutic agent, and retinol, retinol palmitate, and the like which have relatively small irritation to the skin are widely used as a cosmetic material. However, when irradiated with light, retinol and retinol palmitate are denatured by light and have problems of phototoxicity causing irritation to the skin or the stability thereof, and though vitamin C is also a widely used therapeutic agent for reducing wrinkles, it has demerits of causing irritation to the skin due to its strong acidity, and having low stability of the material itself.

Accordingly, development of a new anti-aging cosmetic composition being safe to the body and highly effective, as compared with the conventional anti-aging composition is urgently required.

DISCLOSURE

Technical Problem

An object of the present invention is to provide an anti-aging composition for reducing skin wrinkles and improving skin elasticity.

Another object of the present invention is to provide a method useful for reducing skin wrinkles and improving skin elasticity, by applying the anti-aging composition on the skin to accelerate collagen biosynthesis in the skin.

Technical Solution

In one general aspect, an anti-aging composition includes: a compound represented by the following Chemical Formula 1 as an effective component:

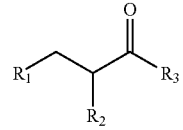

[Chemical Formula 1]

wherein
$R_1$ is hydrogen, (C1-C30) alkyl, (C2-C30) alkenyl, (C2-C30) alkynyl, (C1-C30) alkoxy or hydroxy (C1-C30) alkyl;
$R_2$ is (C1-C30) alkyl, (C2-C30) alkenyl, (C2-C30) alkynyl, (C1-C30) alkoxy or hydroxy (C1-C30) alkyl; and
$R_3$ is

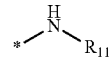

or a substituted or unsubstituted amino acid group, in which $R_{11}$ is hydroxy (C1-C30) alkyl.

The anti-aging composition according to an exemplary embodiment of the present invention provides a new use of the compound which is for reducing skin wrinkles and improving skin elasticity by accelerating collagen biosynthesis.

The present invention provides an in vitro collagen synthesis accelerating agent including a compound represented by the following Chemical Formula 1 as an effective component. Here, the collagen synthesis accelerating agent may refer to a composition for accelerating collagen synthesis.

In addition, the present invention provides a method for reducing skin wrinkles and improving skin elasticity by applying an anti-aging composition including the compound represented by Chemical Formula 1 as an effective component on the skin.

Advantageous Effects

The anti-aging composition according to the present invention has excellent stability, is harmless to the human body, and is superior in the effects of reducing skin wrinkles and improving skin elasticity by accelerating collagen biosynthesis.

BEST MODE

Figure 1:
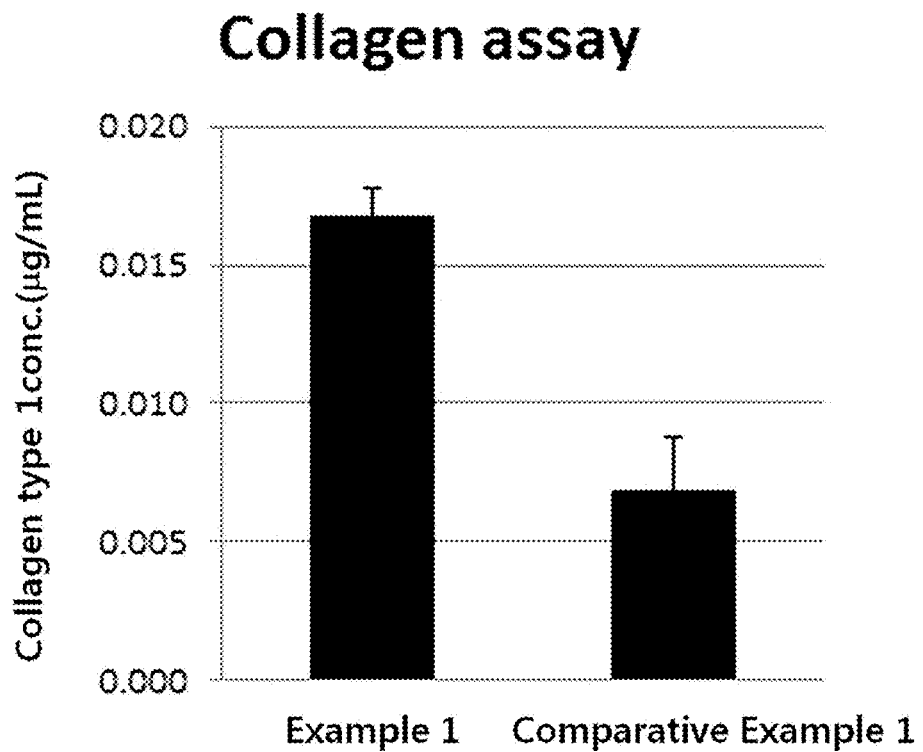
FIG. 1 confirms a value of type-1 collagen following treatment of an anti-aging composition prepared in Example 1.

Hereinafter, the anti-aging composition according to the present invention will be described, however, technical terms and scientific terms used herein have the general meaning understood by those skilled in the art to which the present invention pertains unless otherwise defined, and a description for the known function and configuration obscuring the present invention will be omitted in the following description.

The term used in the present invention, "anti-aging" may be a concept embracing skin protection and improved skin condition, skin whitening, prevention or improvement of skin aging and wrinkles, pore tightening and minimizing, skin protection, an improved skin barrier function, mitigated irritation to the skin, skin cell proliferation and regeneration ability, antioxidant ability, improved collagen synthesis ability, and the like, and in particular, refers to having improved collagen synthesis ability.

The term used in the present invention, "applying" refers to bring the composition according to the present invention into contact with the skin of an individual by an optional appropriate method, which is intended to absorb the composition into the skin.

The term used in the present invention, "prevention" refers to all actions to inhibit or delay occurrence of wrinkles by applying the composition according to the present invention, and the term used in the present invention, "improvement" refers to all actions to improve or change a skin condition favorably, make skin elasticity higher than before, or delay a rate of loss of skin elasticity due to aging, by applying the composition according to the present invention.

The term used in the present invention, "wrinkles" refer to fine lines produced by skin aging, and may be caused by factors by genes, reduced collagen and elastin present in the skin dermis, external environment, and the like. In addition, the term "elasticity" refers to an elastic property represented by elastic fiber composed of elastin present in the dermal layer of the skin, and this elastic fiber has a very low coefficient of elasticity like rubber, thereby being easily denatured only with small power, and when the power is removed, easily returning to an original form. Here, the elastic fiber has the form in which microfibrils are embedded in an amorphous substrate called elastin, and the elastin is a protein composed of a very unique amino acid which is found only in elastic fiber called desmosine and isodesmosine derived from lysine. These desmosine, isodesmosine, and the like forms cross-links in a long peptide chain, and this structure allows elastin to have rubber-like properties.

The present applicant conducted an intensive study on a new raw material showing a strong effect on anti-aging and having excellent formulation stability, and as a result, derived that the compound represented by the following Chemical Formula 1 having an anti-inflammatory effect has effects of reducing skin wrinkles and improving skin elasticity, so that an anti-aging composition including the compound represented by the following Chemical Formula 1 as an effective component is provided, thereby completing the present invention.

[Chemical Formula 1]

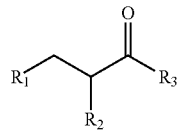

wherein $R_1$ is hydrogen, (C1-C30) alkyl, (C2-C30) alkenyl, (C2-C30) alkynyl, (C1-C30) alkoxy or hydroxy (C1-C30) alkyl;

$R_2$ is (C1-C30) alkyl, (C2-C30) alkenyl, (C2-C30) alkynyl, (C1-C30) alkoxy or hydroxy (C1-C30) alkyl; and $R_3$ is

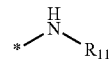

or a substituted or unsubstituted amino acid group, in which $R_{11}$ is hydroxy (C1-C30) alkyl.

The terms, "alkyl", "alkoxy" and other substituents including the "alkyl" part, described herein, include all forms of straight chain or branched chain. In addition, alkyl, alkoxy and hydroxyalkyl according to the present invention are preferentially those having 1 to 7 carbon atoms in a straight chain form, or having a straight chain form of 1 to 7 carbon atoms, however, those having 8 to 30 carbon atoms are also an embodiment of the present invention, of course.

In addition, "alkenyl" described herein is hydrocarbon in a straight chain form or a branched chain form containing one or more double bonds, and an example thereof may include ethenyl, prop-1-en-1-yl, pro-p-1-en-2-yl, prop-2-en-1-yl, prop-2-en-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, and the like, but not limited thereto. "Alkynyl" described herein is hydrocarbon in a straight chain form or a branched chain form containing one or more triple bonds, and an example thereof may include ethynyl, prop-1-yn-1-yl, prop-2-yn-1-yl, but-1-yn-1-yl, but-1-yn-3-yl, but-3-yn-1-yl, and the like, but not limited thereto.

In the anti-aging composition according to an exemplary embodiment of the present invention, the compound has excellent solubility and compatibility with a solvent, is safe to the body, and accelerates biosynthesis of type-1 and type 3 collagens of skin fibroblasts, thereby improving skin elasticity, and in term of having an excellent effect of reducing skin wrinkles, $R_3$ of the compound may be preferably selected from the following structures:

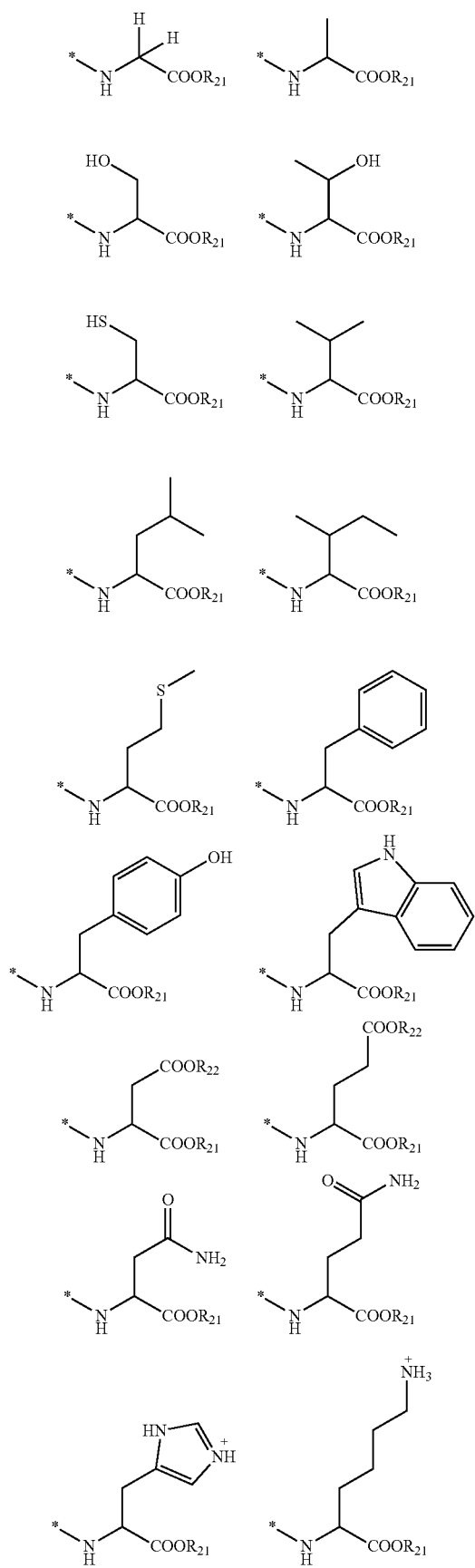

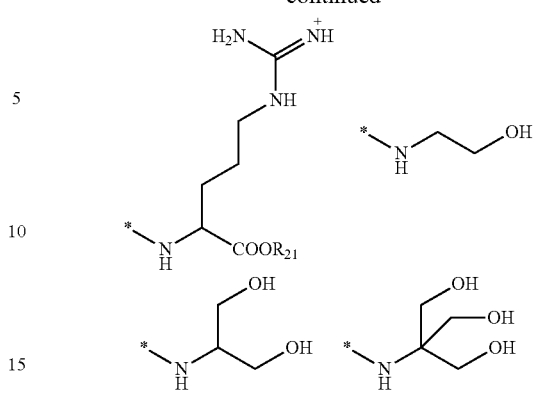

wherein $R_{21}$ to $R_{22}$ are independently of each other hydrogen or (C1-C7) alkyl.

In the anti-aging composition according to an exemplary embodiment of the present invention, it is preferred that $R_{21}$ and $R_{22}$ are independently of each other selected from the group consisting of methyl, ethyl and propyl, but not limited thereto.

The compound according to an exemplary embodiment of the present invention is a very stable material so that a formulation is easily developed, and has no skin side effect such as a skin barrier dysfunction and epidermal hyperplasia, and particularly in terms of having excellent biosynthesis ability of type-1 collagen, more preferably, R3 of the compound may be hydroxy (C3-C4) alkyl in a branched chain form, and as a more preferred example, may be a compound represented by the following Chemical Formula 2, but not limited thereto:

[Chemical Formula 2]

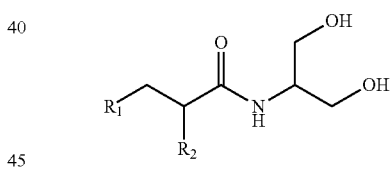

wherein $R_1$ is hydrogen, (C1-C7) alkyl or hydroxy (C1-C7) alkyl; and $R_2$ is (C1-C7) alkyl or hydroxy (C1-C7) alkyl.

In addition, as a result of adding the composition of the present invention to a culture medium of human-derived fibroblasts, and measuring amounts of two types of biosynthesized collagen, the present applicant proved that the compound represented by Chemical Formula 1 and the anti-aging composition including the compound as an effective component are very effective in accelerating biosynthesis of collagen, more particularly type-1 and type-3 collagens, thereby identifying the fact that the compound represented by Chemical Formula 1 and the anti-aging composition including the compound as an effective component are useful for the effects of improving skin elasticity and reducing skin wrinkles. In addition, the present applicant confirmed that the compound represented by Chemical Formula 1 and the anti-aging composition including the compound as an effective component do not show toxicity in a concentration range of not inducing cell proliferation, thereby identifying that the compound and the composition are very safe.

That is, the anti-aging composition according to an exemplary embodiment of the present invention accelerates biosynthesis of collagen as a skin external preparation, thereby exhibiting an effect useful for anti-aging, not causing skin side effects such as a skin barrier dysfunction and epidermal hyperplasia, possessed by retinoid and the like which were conventionally useful for anti-aging, and being very stable to easily develop a formulation, and thus, the composition is expected to be safely and effectively utilized as a cosmetic composition, a pharmaceutical composition, and the like.

The anti-aging composition according to an exemplary embodiment of the present invention, such as a cosmetic composition and a pharmaceutical composition includes the compound as an effective component preferably at 0.001 to 50 wt %, and more preferably 0.01 to 30.0 wt %, based on the total weight of the composition, but not limited thereto.

Hereinafter, the anti-aging cosmetic composition according to an embodiment of the present invention will be described in detail.

The cosmetic composition according to the present invention may further include one or more wrinkle reducing components selected from the group consisting of retinoic acid, TGF, protein derived from an animal placenta, betulinic acid and a chlorella extract, as a wrinkle reducing component known in the art, of course, for improving anti-aging, together with the compound. Here, the further wrinkle reducing component may be included at 0.000001 wt % to 10 wt %, based on the total weight of the cosmetic composition, and the wt % may be adjusted depending on the requirements such as collagen synthesis acceleration activity, skin safety, and ease of formulation with the compound represented by Chemical Formula 1.

In addition, the cosmetic composition according to an exemplary embodiment of the present invention may include one or more additives selected from one or more aqueous additives selected from the group consisting of purified water, a stabilizer, an emulsifier, a thickening agent, a moisturizer, a liquid crystal film enhancer, a pH controlling agent, an antimicrobial, an aqueous polymer, a coating agent, a metal ion sequestering agent, amino acid, organic amine, polymer emulsion, a pH adjusting agent, a skin nutrient, an anti-oxidant, an anti-oxidant auxiliary agent, a preservative, flavoring, and the like; and one or more oil-based additives selected from the group consisting of fat and oils, waxes, hydrocarbon oil, higher fatty acid oil, higher alcohol, synthetic ester oil, silicone oil, and the like.

Here, the aqueous additive is not limited, as long as it is generally used in the art, and a specific example thereof may be one or more selected from the group consisting of glycerin, dipropyleneglycol, butyleneglycol, pentyleneglycol, methyl propanediol, sorbitol, diglycerin, erythritol, pentaerythritol, polybutyleneglycol-10, polyglycerin-3, polyglycerin-4, polyglycerin-6, polyglycerin-10, polyglycerin-20, polyglycerin-40, sorbeth-5, sorbeth-6, sorbeth-20, sorbeth-30, sorbeth-40, inositol, maltitol, maltose, mannitol, mannose, lactitol, lactose, dihydroxypropyl PG-glucoside, dithiaoctanediol, fructose, glucamine, methyl glucamine, glucose, 1,2,6-hexanethiol, methyl gluceth-10, methyl gluceth-20, ozonized glycerin, phytantriol, thiglycerin, threitol, trimethylolpropane, xylitol, EDTA, guar gum, quince seeds, carrageenan, galactan, arabic gum, pectin, mannan, starch, xanthan gum, curdlan, methyl cellulose, hydroxy ethyl cellulose, carboxymethyl cellulose, methyl hydroxypropyl cellulose, chondroitin sulfate, dermatan sulfate, glycogen, heparan sulfate, hyaluronic acid, sodium hyaluronate, tragacanth gum, keratan sulfate, chondroitin, mucoitin sulfate, hydroxyethyl guar gum, acrboxymethyl guar gum, dextran, kerat sulfate, locust bean gum, succinoglucan, caronic acid, chitin, chitosan, carboxymethyl chitin, agar, polyvinyl alcohol, polyvinyl pyrrolidone, carboxyvinyl polymer, sodium polyacrylate, polyethylene glycol, bentonite, methylparaben, propylparaben, phenoxyethanol, 1,2-hexanediol, ethylhexyl glycerin, and the like. In addition, the oil-based additive is not limited, as long as it is a raw material generally used in the art, and may be for example, liquid oils such as olive oil, camellia oil, jojoba oil, triglyceride, glycerin trioctanoate and glycerin triisopalmitate, solid oils such as palm oil, hydrogenated palm oil, hydrogenated oil and hydrogenated castor oil, beeswax, candelilla wax, carnauba wax, lanolin, jojoba wax, and the like. An example of the hydrocarbon oil includes liquid paraffin, squalene, petrolatum, microcrystalline wax, and the like. An example of the higher fatty acid may be waxes such as lauric acid, myristic acid, palmitic acid, stearic acid and behenic acid, cetyl alcohol, stearyl alcohol, behenyl alcohol, myristyl alcohol, cetosteryl alcohol, and the like; the synthetic ester oil may be selected from the group consisting of higher alcohol such as isopropyl myristate, cetyl octanoate, octyldodecyl myristate, isopropyl palmitate, hexyl laurate, myristyl myristate, cetyl lactate, isocetyl isostearate, neopentyl glycol dicaprate, ethylhexyl glycerin, cetylethyl hexanoate, ethylhexyl palmitate and cetostearyl alcohol, chain type silicone oil such as dimethyl polysiloxane, methylphenyl polysiloxane and methylhydrdogenpolysiloxane, cyclic silicone oil such as dodecamethylcyclohexasiloxane and octamethylcyclotetrasiloxane, decamethylcyclopentasiloxane, and the like, but not limited thereto.

The cosmetic composition according to an exemplary embodiment of the present invention may be prepared in the form of a general emulsion formulation and a solubilized formulation, of course, using a preparation method commonly known in the art, in addition to the preparation method particularly disclosed in the present invention. Here, the cosmetic composition may be properly selected according to the purpose, and as a specific example thereof, the composition may be formulated into the formulation selected from the group consisting of an emollient, an astringent, a nutritional toner, an eye cream, a nourishing cream, a massage cream, a cleansing cream, a cleansing foam, a cleansing water, powder, an essence, a face pack, and the like, but not limited thereto.

Hereinafter, the anti-aging pharmaceutical composition according to one embodiment of the present invention will be described in detail.

The anti-aging pharmaceutical composition according to an exemplary embodiment of the present invention may include a pharmaceutically acceptable carrier, according to the method which may be easily carried out by a person having ordinary skill in the art to which the invention pertains. The pharmaceutically acceptable carrier included in the anti-aging pharmaceutical composition of the present invention is commonly used in preparation, and may be lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, or mineral oil, but not limited thereto. The anti-aging pharmaceutical composition of the present invention may further include a lubricant, a wetting agent, a sweetener, a flavoring agent, an emulsifier, a suspending agent, a preservative and the like, in addition to the above components.

The pharmaceutical composition according to an exemplary embodiment of the present invention may be prepared using a commonly known preparation method, of course, in addition to the preparation method particularly disclosed in the present invention, and may be formulated into an appropriate form as desired. As a specific example thereof, forms such as a lotion, an ointment, a gel, a cream, a patch and a spraying agent may be listed, but not limited thereof.

An embodiment of the present invention provides a collagen synthesis accelerating agent including the compound represented by the following Chemical Formula 1 as an effective component.

In addition, an embodiment of the present invention provides a method for reducing skin wrinkles and improving skin elasticity by applying an anti-aging composition including the compound represented by Chemical Formula 1 as an effective component on the skin.

Hereinafter, preferred exemplary embodiments will be provided in order to assist understanding of the present invention. However, the following Examples are only provided for easily understanding the present invention, and only illustrative, but do not limit the scope of the present invention in any way.

EXAMPLE 1

N-(1,3-dihydroxy propan-2-yl)-2-ethylhexanamide was added to a culture medium of human fibroblasts (DMEM medium, 10% fetal bovine serum, 1% antibiotics) to confirm the effect of accelerating type-1 collagen synthesis in a cell level. The measurement of the synthesized collagen was qualified using a procollagen type I C-peptide enzyme immunoassay kit (PICP EIA kit).

The human fibroblast culture medium was used to aliquot the human-derived fibroblasts (human fibroblasts) into 6 wells at $2\times10^5$ cell/well. After cell adhesion was confirmed, the culture medium was treated with 2 ml of N-(1,3-dihydroxy propan-2-yl)-2-ethylhexanamide as an effective component (anti-aging composition) per each well, at a concentration of 20 uM. After the culture medium was cultured in an incubator under a condition of 37° C. and 5% $CO_2$ for 24 hours, type-1 collagen which is related to a wrinkle forming factor was measured in a cell extract. Here, the concentration of the anti-aging composition is within a range being not toxic and not deriving cell proliferation, when treating human-derived fibroblasts. The results were illustrated in Table 1 and FIG. 1.

EXAMPLE 2

Artificial skin (EpiDermFT™ from MatTek, Ashland, USA) was purchased, and stabilized in an exclusive medium (EFT-400) for 18 hours. On the surface of the artificial skin, 100 μl of N-(1,3-dihydroxy propan-2-yl)-2-ethylhexanamide as an effective component (anti-aging composition) at a concentration of 1% was applied. After 24 hours, the artificial skin tissue was immobilized with 10% formaldehyde, embedded with paraffin, and sliced at 5 μm to obtain a sliced tissue which was used for confirming the effect of accelerating collagen synthesis (see FIG. 2).

COMPARATIVE EXAMPLE 1

The effect of accelerating type-1 collagen synthesis was confirmed in the same manner as in Example 1, except that the effective component was not used (a negative control). In addition, type-1 collagen synthesis ability relative to the negative control was calculated as a ratio, and illustrated as a rate of increase (see Table 1 and FIG. 1).

COMPARATIVE EXAMPLE 2

The artificial skin was stabilized in the same manner as in Example 2, and coated with only 100 μl of PBS without an effective component. After 24 hours, the artificial skin tissue was immobilized with 10% formaldehyde, embedded with paraffin, and sliced at 5 μm to obtain a sliced tissue which was used for confirming the effect of accelerating collagen synthesis.

TABLE 1

|  | Example 1 | Comparative Example 1 |
|---|---|---|
| Type-1 collagen concentration (20 uM) | 0.017 | 0.007 |
| Rate of increase (%) | 242 | — |

As a result of confirming the effect of accelerating type-1 collagen synthesis as described above, it was found that a rate of increase up to 242% was shown as compared with Comparative Example 1 (the negative control). That is, it was found that the effect of increasing type-1 collagen of the anti-aging composition according to the present invention was significantly increased, with the value of type-1 collagen which was significantly increased as compared with Comparative Example 1.

Figure 2:
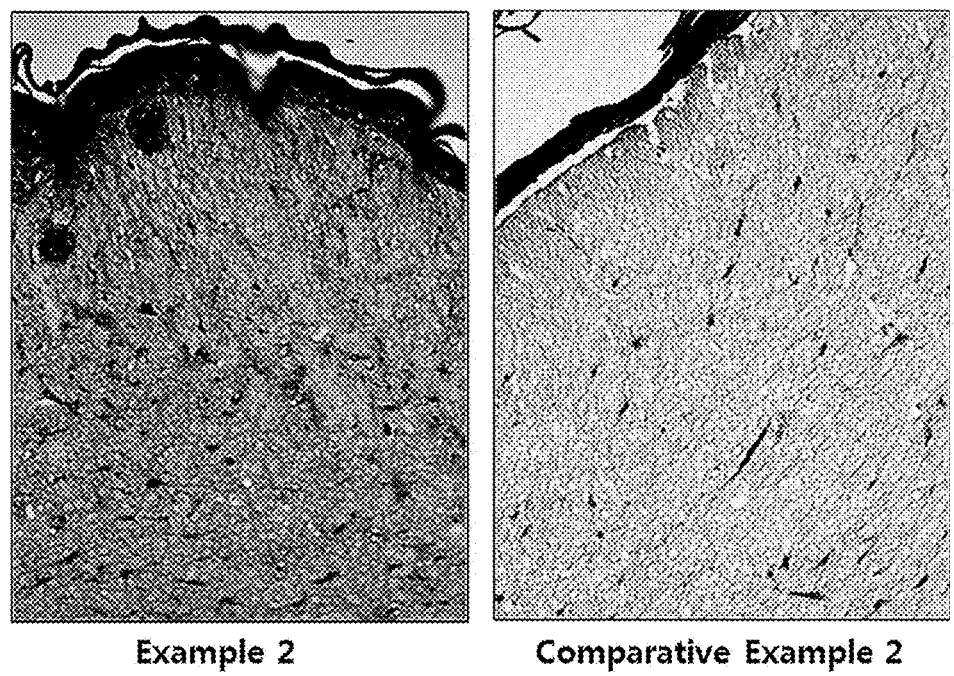
FIG. 2 is a result of Masson's Trichrome staining for measuring an amount of collagen expression in dermis tissue following treatment of an anti-aging composition prepared in Example 2.

In addition, as illustrated in FIG. 2, as a result of staining the collagen of the artificial skin tissue using a Masson's Trichrome staining method for confirming the effect of accelerating collagen synthesis, it was found that the tissue coated with Example 2 accelerated collagen synthesis much more in the artificial skin tissue as compared with Comparative Example 2.

Accordingly, the anti-aging composition according to the present invention accelerates collagen fiber synthesis, thereby excelling in preventing skin aging and reducing skin wrinkles, and thus, it is expected to utilize the composition in various formulations.

The present invention has been described in detail in specific parts, and it is obvious that such specific technique is only an embodiment to a person skilled in the art, without limiting the scope of the present invention thereto. Thus, the substantial scope of the present invention will be defined by the appended claims and their equivalents.

The invention claimed is:
1. A method for reducing skin wrinkles and improving skin elasticity by applying an anti-aging composition comprising a compound represented by Chemical Formula 1 as an effective component on skin to a human in need thereof:

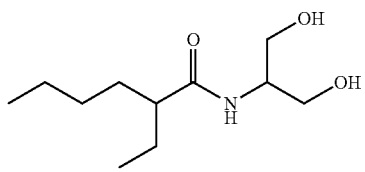

2. The method of claim 1, wherein the compound is comprised at 0.001 to 50 wt %, based on a total weight of the composition.

* * * * *